United States Patent
Böhringer et al.

(10) Patent No.: US 10,532,071 B2
(45) Date of Patent: Jan. 14, 2020

(54) HIGH-PERFORMANCE ADSORBENTS BASED ON ACTIVATED CARBON HAVING HIGH MESO- AND MACROPOROSITY

(71) Applicant: Blücher GmbH, Erkrath (DE)

(72) Inventors: Bertram Böhringer, Wuppertal (DE); Sven Fichtner, Brandenburg (DE); Jann-Michael Giebelhausen, Rathenow (DE)

(73) Assignee: Blücher GmbH, Erkrath (DE)

( * ) Notice: Subject to any disclaimer, the term of this patent is extended or adjusted under 35 U.S.C. 154(b) by 121 days.

(21) Appl. No.: 15/862,007

(22) Filed: Jan. 4, 2018

(65) Prior Publication Data

US 2018/0125886 A1    May 10, 2018

Related U.S. Application Data

(63) Continuation of application No. 12/595,728, filed as application No. PCT/EP2008/000606 on Jan. 25, 2008, now abandoned.

(30) Foreign Application Priority Data

Mar. 14, 2007   (DE) .................. 10 2007 012 963
Oct. 25, 2007   (DE) .................. 10 2007 050 971

(51) Int. Cl.
| C01B 31/10 | (2006.01) |
| A61K 33/44 | (2006.01) |
| C01B 32/354 | (2017.01) |
| C01B 32/336 | (2017.01) |
| A61L 9/014 | (2006.01) |
| B01D 53/02 | (2006.01) |
| B01J 20/20 | (2006.01) |
| B01J 20/28 | (2006.01) |
| C01B 32/318 | (2017.01) |
| C02F 1/28 | (2006.01) |

(52) U.S. Cl.
CPC ............. *A61K 33/44* (2013.01); *A61L 9/014* (2013.01); *B01D 53/02* (2013.01); *B01J 20/20* (2013.01); *B01J 20/28019* (2013.01); *B01J 20/28057* (2013.01); *B01J 20/28076* (2013.01); *B01J 20/28083* (2013.01); *B01J 20/28085* (2013.01); *C01B 32/318* (2017.08); *C01B 32/336* (2017.08); *C01B 32/382* (2017.08); *B01D 2253/10* (2013.01); *B01D 2253/102* (2013.01); *B01D 2253/306* (2013.01); *B01D 2253/311* (2013.01); *C02F 1/283* (2013.01); *Y02C 10/08* (2013.01)

(58) Field of Classification Search
CPC .................................................. C01B 32/318
See application file for complete search history.

(56) References Cited

U.S. PATENT DOCUMENTS

| 4,761,284 A | 8/1988 | Nishimura |
| 4,937,223 A | 6/1990 | Yamaguchi |
| 5,242,879 A | 9/1993 | Abe et al. |
| 6,114,280 A | 9/2000 | Stephens |
| 6,865,068 B1 | 3/2005 | Murakami et al. |
| 7,737,083 B2 * | 6/2010 | von Blucher .......... A61K 33/44 502/416 |
| 8,227,376 B2 | 7/2012 | Karles et al. |
| 2006/0148645 A1 | 7/2006 | Schonfeld et al. |
| 2007/0054580 A1 | 3/2007 | Sakurai et al. |

FOREIGN PATENT DOCUMENTS

| DE | 918800 | 10/1954 |
| DE | 20319676 | 1/2005 |
| DE | 102005062160 | 6/2007 |
| DE | 202006011163 | 8/2007 |
| DE | 102006022178 | 10/2007 |
| DE | 102006023155 | 11/2007 |
| EP | 1666649 | 1/1986 |
| EP | 1004001 | 5/2000 |
| EP | 1049116 | 11/2000 |
| EP | 1797889 | 6/2007 |
| EP | 1847318 | 10/2007 |
| JP | 57061601 | 4/1982 |
| JP | 61151012 | 7/1986 |
| JP | 06009208 | 1/1994 |
| JP | 08040713 | 5/1995 |
| JP | 10297912 | 11/1996 |
| JP | 2001089119 | 4/2001 |
| JP | 2004182511 | 7/2004 |
| JP | 2005518475 | 6/2005 |
| JP | 2007002709 | 6/2005 |
| JP | 2006131461 | 5/2006 |
| KR | 20010055177 | 7/2001 |
| WO | 9909365 | 2/1999 |
| WO | 9936864 | 7/1999 |
| WO | 03072682 | 9/2003 |
| WO | 2004046033 | 6/2004 |

* cited by examiner

*Primary Examiner* — Stuart L Hendrickson
(74) *Attorney, Agent, or Firm* — Edward E. Sowers; Brannon Sowers & Cracraft PC

(57) ABSTRACT

The invention concerns high-performance adsorbents based on activated carbon of high meso- and macroporosity which are present in the form of discrete grains of activated carbon, wherein:
   at least 55% of the total pore volume of the high-performance adsorbents are formed by pores (i.e. meso- and macropores) having pore diameters of more than 20 Å,
   the high-performance adsorbents have a measure of central tendency pore diameter of more than 25 Å, and
   the high-performance adsorbents have a BET surface area of at least 1250 m$^2$/g.
These high-performance adsorbents are obtainable by a novel process comprising specific two-stage activation, and have, in addition to the aforementioned properties, an excellent abrasion and bursting resistance, so that they are useful for a multiplicity of different applications.

13 Claims, 2 Drawing Sheets

HIGH-PERFORMANCE ADSORBENTS BASED ON ACTIVATED CARBON HAVING HIGH MESO- AND MACROPOROSITY

CROSS-REFERENCES TO RELATED APPLICATIONS

This patent application is a continuation of U.S. application Ser. No. 12/595,728, entitled "HIGH-PERFORMANCE ADSORBENTS BASED ON ACTIVATED CARBON HAVING HIGH MESO- AND MACROPOROSITY" filed on May 31, 2011, which claims priority to PCT/EP2008/000606, filed Jan. 25, 2008, and to German Applications DE 10 2007 012 963.9 filed Mar. 14, 2007 and DE 10 2007 050 971.7, filed Oct. 25, 2007, and incorporates all by reference herein, as if each one were independently incorporated in its entirety.

BACKGROUND OF THE INVENTION

The present invention concerns the adsorption arts. More particularly, the present invention concerns high-performance adsorbents based on activated carbon of high meso- and macroporosity and a process for production thereof and also the use of these high-performance adsorbents, particularly for adsorptive filtering materials, for the food industry (for example for preparing and/or decolorizing food products, for the adsorption of toxins, noxiants and odors, particularly from gas or air streams, for purifying or cleaning gases, particularly air, and liquids, particularly water, for application in medicine or to be more precise pharmacy, and also as sorptive storage media particularly for gases, liquids and the like.

Activated carbon has fairly unspecific adsorptive properties and therefore is the most widely used adsorbent. Legislation as well as the rising sense of responsibility for the environment lead to a rising demand for activated carbon.

Activated carbon is generally obtained by carbonization (also referred to by the synonyms of smoldering, pyrolysis, burn-out, etc) and subsequent activation of carbonaceous compounds, preferably such compounds as lead to economically reasonable yields. This is because the weight losses through detachment of volatile constituents in the course of carbonization and through the subsequent burn-out in the course of activation are appreciable. For further details concerning the production of activated carbon, see for example H.v. Kienle and E. Bäder, Aktivkohle and ihre industrielle Anwendung, Enke Verlag Stuttgart, 1980.

The constitution of the activated carbon produced—finely or coarsely porous, firm or brittle, etc—depends on the starting material. Customary starting materials are coconut shells, charcoal and wood (for example wood wastes), peat, bituminous coal, pitches, but also particular plastics which play a certain part in the production of woven activated carbon fabrics for example.

Activated carbon is used in various forms: pulverized carbon, splint coal carbon, granulocarbon, molded carbon and also, since the end of the 1970s, spherical activated carbon ("spherocarbon"). Spherical activated carbon has a number of advantages over other forms of activated carbon such as pulverized carbon, splint coal carbon, granulocarbon, molded carbon and the like that make it useful or even indispensable for certain applications: it is free flowing, abrasion resistant or to be more precise dustless, and hard. Spherocarbon is in great demand for particular applications, for example, because of its specific form, but also because of its high abrasion resistance.

Spherocarbon is mostly still being produced today by multistage and very costly and inconvenient processes. The best known process consists in producing spherules from bituminous coal tar pitch and suitable asphaltic residues from the petrochemical industry, which are oxidized to render them unmeltable and then smoldered and activated. For example, spherocarbon can also be produced in a multistage process proceeding from bitumen. These multistage processes are very cost intensive and the associated high cost of this spherocarbon prevents many applications wherein spherocarbon ought to be preferable by virtue of its properties.

WO 98/07655 A1 describes a process for producing activated carbon spherules wherein a mixture comprising a diisocyanate production distillation residue, a carbonaceous processing aid and if appropriate one or more further additives is processed into free-flowing spherules and subsequently the spherules obtained in this way are carbonized and then activated.

It is further prior art to produce spherocarbon by smoldering and subsequent activation of new or used ion exchangers comprising sulfonic acid groups, or by smoldering ion exchanger precursors in the presence of sulfuric acid and subsequent activation, the sulfonic acid groups and the sulfuric acid respectively having the function of a cross-linker. Such processes are described for example in DE 43 28 219 A1 and DE 43 04 026 A1 and also in DE 196 00 237 A1 including the German patent-of-addition application DE 196 25 069 A1.

However, there are a number of specific applications where it is not only the geometry or to be more precise the external shape of the activated carbon which is of decisive importance, but also its porosity, in particular the total pore volume and the adsorption capacity on the one hand and the distribution of the pores, i.e., the fraction of micro-, meso- and macropores in relation to the total pore volume, on the other.

There are a number of applications requiring a particularly high meso- and macroporosity of the activated carbon, i.e., a high meso- and macropore volume fraction, coupled with an altogether high total pore volume, for example in relation to the applications mentioned at the beginning, for example for use in the food industry, in the manufacture of certain adsorptive filtering materials (for example for NBC protective apparel), for the adsorption of toxins, noxiants and odors, particularly from gas or air streams, for purifying or cleaning gases, such as in particular air, and also liquids, for application in medicine or to be more precise pharmacy, in the sorptive storage of gases or liquids and the like.

True, the activated carbon known for this purpose from the prior art does have a certain degree of meso- and macroporosity, but that degree is not sufficient in all cases. In addition, increasing porosity is often observed to be accompanied by an unwelcome, occasionally unacceptable decrease in mechanical stability or to be more precise abrasion resistance. Nor are the fraction of the total pore volume which is accounted for by meso- and macropores and the absolute pore volume always sufficient to ensure adequate performance capability and/or an adequate impregnatability (for example impregnation with metals or metal salts) for all applications.

BRIEF SUMMARY OF THE INVENTION

This invention relates to high-performance adsorbents based on activated carbon in the form of discrete grains of activated carbon having: (a) at least 70% of the total pore volume formed by pores having pore diameters of more than 20 Å; (b) a measure of central tendency pore diameter (mean pore diameter) of more than 25 Å; (c) a BET surface area of at least 1,250 m$^2$/g; and (d) an iodine number of at least 1,250 mg/g. Such adsorbents typically have a high meso- and macroporosity, (i.e. a high meso- and macroporous fraction relative to the total pore volume), a large total pore volume and yet retain high stability to abrasion and bursting.

Further aspects of the present invention relate to a process for producing the high-performance adsorbents based on activated carbon. The process utilizes a carbonaceous starting material and involves initially carbonizing and subsequently activating the starting material. The activation step is carried out in two stages. The carbonized starting material is initially subjected, in a first activating step in an atmosphere of water vapor, followed by a second activation step in an atmosphere that includes $CO_2$.

Further aspects of the present invention relate to a filtering material based on the high-performance adsorbents described above.

Still further aspects of the present invention relate to a piece of protective apparel that includes the high-performance adsorbents described above.

DETAILED DESCRIPTION OF THE INVENTION

Figure 1:
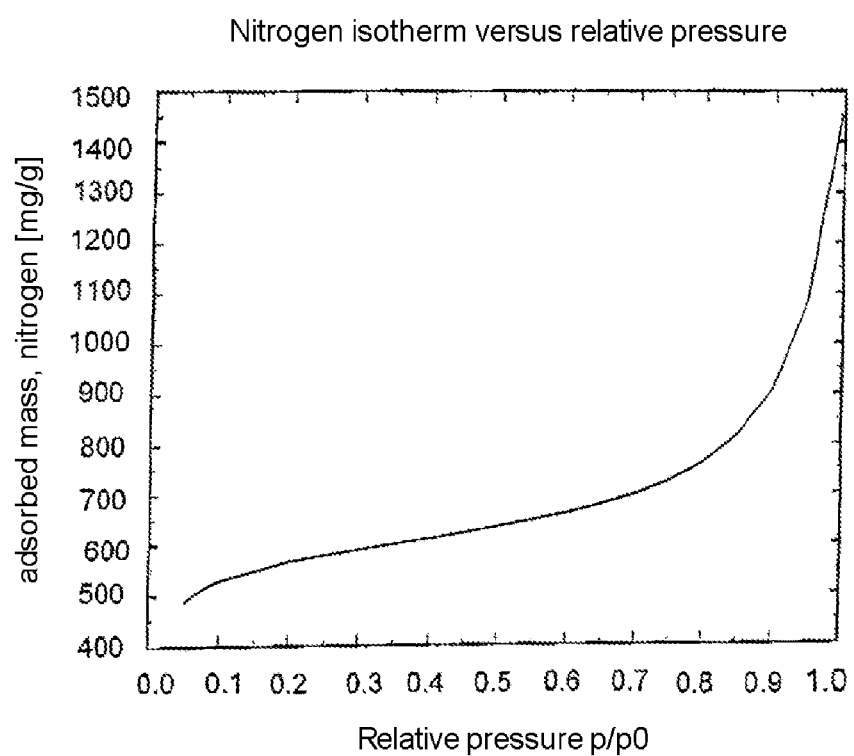
FIG. 1 is a graph illustrating a $N_2$ adsorption isotherm for a first high-performance adsorbent of the present invention.

It is therefore an object of the present invention to provide, on the basis of activated carbon, a high-performance adsorbent which is suitable for the aforementioned fields of application in particular and which at least substantially avoids or else at least ameliorates the above-described disadvantages of the prior art. More particularly, the adsorbent to be provided according to the present invention should have a high meso- and macroporosity, i.e., a high meso- and macroporous fraction in relation to the total pore volume and also a large total pore volume, yet at the same time also good mechanical stability, particularly a high stability to abrasion and bursting.

In the context of the present invention, the term "micropores" refers to pores having pore diameters of up to 20 Å inclusive, whereas the term "mesopores" refers to pores having pore diameters in the range of more than 20 Å (i.e., >20 Å) to 500 Å inclusive and the term "macropores" refers to pores having pore diameters of more than 500 Å (i.e., >500 Å):

micropores: pore diameter$_{micropores}$ ≥ 20 Å
mesopores: 20 Å < pore diameter$_{mesopores}$ ≤ 500 Å
macropores: pore diameter$_{macropores}$ > 500 Å

By way of a solution to the problem described above, the present invention proposes—in accordance with a first aspect of the present invention—high-performance adsorbents based on activated carbon in the form of discrete grains of activated carbon, preferably in spherical form, according to claim 1. Further, in particular advantageous embodiments of the high-performance adsorbents of the present invention are subject matter of the corresponding subclaims.

The present invention further provides—in accordance with a second aspect of the present invention—the present invention process for producing the high-performance adsorbents according to the present invention, as more particularly defined in the corresponding process claims.

The present invention yet further provides—in accordance with a third aspect of the present invention—the present invention use of the high-performance adsorbents according to the present invention, as more particularly defined in the corresponding use claims.

The present invention accordingly provides—in accordance with a first aspect of the present invention—high-performance adsorbents based on activated carbon in the form of discrete grains of activated carbon, preferably in spherical form, these high-performance adsorbents being characterized by the following parameters:

a pore volume fraction formed by pores having pore diameters of more than 20 Å (i.e., in other words, a meso- and macropore volume fraction) which comprises at least 55% of the total pore volume of high-performance adsorbents (This parameter is interchangeably also referred to as "fraction of external pore volume in relation to total pore volume".), a measure of central tendency pore diameter of more than 25 Å.

a BET surface area of at least 1250 m$^2$/g,

The present high-performance adsorbents or to be more precise activated carbons, in addition to the aforementioned properties or to be more precise parameters, particularly a high meso- and macropore volume fraction (i.e., a high pore volume fraction due to pores having a pore diameter of more than 20 Å), are further notable in particular for a large total porosity and a simultaneously large BET surface area.

As will be shown in what follows, the mechanical strength, particularly the abrasion resistance and the bursting or to be more precise compressive strength, of the present high-performance adsorbents is despite the high total porosity extremely high—in contrast to comparable high-porosity activated carbons of the prior art—so that the present high-performance adsorbents or to be more precise activated carbons are also suitable for applications where they are exposed to large mechanical loads.

In relation to all the parameter indications hereinabove and hereinbelow, it is to be noted that the recited limits, in particular upper and lower limits, are included, i.e., all statements of values are to be understood as including the respective limits, except where otherwise stated in an individual case. It will further be understood that in an individual case or in relation to an application it may be necessary if appropriate to depart slightly from the limits mentioned without leaving the realm of the present invention.

The hereinabove and hereinbelow mentioned parameter data are determined using standardized or explicitly indicated methods of determination or using methods of determination familiar per se to one skilled in the art.

The parameter data concerning the characterization of the porosity, particularly of the above-specified meso- and macropore fraction (i.e., the fraction of the total pore volume of the high-performance adsorbents which is contributed by pores having pore diameters of more than 20 Å) each follow from the nitrogen isotherm of the activated carbon measured.

The measure of central tendency pore diameter is similarly determined on the basis of the respective nitrogen isotherms.

The BET method of determining the specific surface area is in principle known as such to one skilled in the art, so that no further details need be furnished in this regard. All BET surface area data are based on the ASTM D6556-04 method of determination. The present invention utilizes the Multi-Point BET (MP-BET) method of determination in a partial pressure range $p/p_0$ of 0.05 to 0.1.

With regard to further details concerning the determination of the BET surface area or to be precise concerning the BET method, reference may be made to the aforementioned ASTM D6556-04 standard and also to Römpp Chemielexikon, 10th edition, Georg Thieme Verlag, Stuttgart/New York, headword: "BET-Methode", including the references cited therein, and to Winnacker-Küchler (3rd edition), Volume 7, pages 93 ff, and also to Z. Anal. Chem. 238, pages 187 to 193 (1968).

As observed above and more particularly specified hereinbelow, one special feature of the high-performance adsorbents of the present invention is that they have a very large total pore volume as determined by the Gurvich method, to provide a very large adsorptive capacity in which the meso- and macropore volume fraction (i.e., that is, the pore volume fraction due to pores having pore diameters above 20 Å) is high, viz. at least 55% of the total pore volume.

The Gurvich determination of total pore volume is a method of measurement/determination known per se in this field to a person skilled in the art. For further details concerning the Gurvich determination of total pore volume reference may be made for example to L. Gurvich (1915), J. Phys. Chem. Soc. Russ. 47, 805, and also to S. Lowell et al., Characterization of Porous Solids and Powders: Surface Area Pore Size and Density, Kluwer Academic Publishers, Article Technology Series, pages 111 et seq.

The Gurvich total pore volume of the high-performance adsorbents of the present invention is at least 0.8 cm$^3$/g, particularly at least 1.0 cm$^3$/g, preferably at least 1.2 cm$^3$/g, and can generally attain values of up to 2.0 cm$^3$/g, particularly up to 2.5 cm$^3$/g, preferably up to 3.0 cm$^3$/g, more preferably up to 3.5 cm$^3$/g.

The Gurvich total pore volume of the high-performance adsorbents of the present invention is generally in the range from 0.8 to 3.5 cm$^3$/g, particularly 1.0 to 3.5 cm$^3$/g, preferably 1.2 to 3.2 cm$^3$/g.

Owing to their high meso- and macroporosity, the meso- and macropore volume of the high-performance adsorbents of the present invention (i.e., that is, in other words, the pore volume formed by pores having pore diameters of more than 20 Å) is relatively high in that in general the carbon black method pore volume of the high-performance adsorbents of the present invention which is formed by pores having pore diameters of more than 20 Å (i.e., that is, the meso- and macropore volume) is in the range from 0.4 to 3.3 cm$^3$/g, particularly 0.8 to 3.2 cm$^3$/g, preferably 1.0 to 3.1 cm$^3$/g, more preferably 1.2 to 3.0 cm$^3$/g, most preferably 1.2 to 2.8 cm$^3$/g. The pore volume formed by pores having pore diameters of more than 20 Å is interchangeably also referred to as "external pore volume".

Generally at least 60%, particularly at least 65%, preferably at least 70%, more preferably at least 75%, most preferably at least 80% of the total pore volume of the high-performance adsorbents of the present invention is formed by the pore volume of pores having pore diameters of more than 20 Å (i.e., that is, in other words, by the meso- and macropore volume).

Generally 55% to 95%, particularly 60% to 95%, preferably 65% to 90%, more preferably 70 to 85% of the total pore volume of the high-performance adsorbents of the present invention is formed by the pore volume of pores having pore diameters of more than 20 Å. The aforementioned percentages thus identify that proportion of the total pore volume of the high-performance adsorbents of the present invention which is attributable to the fraction of the so-called external pore volume (i.e., the pore volume formed by pores having pore diameters of more than 20 Å).

The carbon black method of determination is known per se to one skilled in the art (as is the corresponding analysis, including plotting and fixing of the $p/p_0$ range), so that no further details are needed in this regard. In addition, for further details of the carbon black method of determining the pore surface area and the pore volume reference may be made for example to R. W. Magee, Evaluation of the External Surface Area of Carbon Black by Nitrogen Adsorption, Presented at the Meeting of the Rubber Division of the American Chem. Soc., October 1994, for example cited in: Quantachrome Instruments, AUTOSORB-1, AS1 WinVersion 1.50, Operating Manual, OM, 05061, Quantachrome Instruments 2004, Florida, USA, pages 71 ff.

Owing to the high meso- and macroporosity of the high-performance adsorbents of the present invention, the measure of central tendency pore diameter is relatively high in that in general it is at least 30 Å, particularly at least 35 Å, preferably at least 40 Å.

In general, the measure of central tendency pore diameter of the high-performance adsorbents of the present invention is in the range from 25 to 75 Å, particularly 30 to 75 Å, preferably 35 to 70 Å, more preferably 40 to 65 Å.

As stated above, it is a further special feature of the high-performance adsorbents of the present invention that BET surface area is relatively large and that it is at least 1250 m$^2$/g, preferably at least 1400 m$^2$/g, more preferably at least 1500 m$^2$/g, most preferably at least 1600 m$^2$/g.

In general, the BET surface area of the high-performance adsorbents of the present invention is in the range from 1250 m$^2$/g to 2800 m$^2$/g, particularly 1400 to 2500 m$^2$/g, preferably 1500 to 2300 m$^2$/g, more preferably 1600 to 2100 m$^2$/g.

The carbon black method external pore surface area of the high-performance adsorbents of the present invention (i.e., that is, the pore surface area formed by pores having pore diameters of more than 20 Å) is relatively large, because of the high meso- and macropore fraction, and is generally in the range from 200 to 1000 m$^2$/g, particularly 250 to 950 m$^2$/g, preferably 350 to 900 m$^2$/g, more preferably 400 to 850 m$^2$/g.

In general, the carbon black method external pore surface area of the high-performance adsorbents of the present invention (i.e., that is, the pore surface area formed by pores having pore diameters of more than 20 Å) forms up to 30%, particularly up to 40%, preferably up to 50% of the total pore surface area of the high-performance adsorbents of the present invention. More particularly, the carbon black method external pore surface area of the high-performance adsorbents of the present invention (i.e., that is, the pore surface area formed by pores having pore diameters of more than 20 Å) forms 10 to 50%, particularly 15 to 45%, preferably 20 to 40% of the total pore surface area of the high-performance adsorbents of the present invention.

In addition, the high-performance adsorbents of the present invention have an extremely high butane adsorption and simultaneously an extremely high iodine number, which fact characterizes their property of having excellent adsorption properties with regard to a wide variety of materials to be adsorbed.

The ASTM D5742-95/00 butane adsorption of the high-performance adsorbents of the present invention is generally at least 30%, particularly at least 35%, preferably at least 40%. In general, the high-performance adsorbents of the present invention have an ASTM D5742-95/00 butane adsorption in the range from 30% to 80%, particularly 35 to 75% preferably 40 to 70%.

The ASTM D4607-94/99 iodine number of the high-performance adsorbents of the present invention is generally at least 1250 mg/g, particularly at least 1300 mg/g, preferably at least 1350 mg/g. The high-performance adsorbents of the present invention preferably have an ASTM D4607-94/99 iodine number in the range from 1250 to 2100 mg/g, particularly 1300 to 2000 mg/g, preferably 1350 to 1900 mg/g.

The iodine number can be taken as a measure for available surface area provided by predominantly larger micropores; the aforementioned values of the iodine number of the high-performance adsorbents of the present invention show that the high-performance adsorbents of the present invention simultaneously also have a high microporosity.

Owing to their high meso- and macroporosity, the high-performance adsorbents of the present invention similarly have high methylene blue and molasses adsorption numbers which together can be taken as a measure of available surface area provided predominantly by meso- and macropores. The methylene blue number or to be more precise the methylene blue adsorption, which indicates the amount of methylene blue adsorbed per defined amount of adsorbents, under defined conditions (i.e., the number of ml of a methylene blue standard solution decolorized by a defined amount of dry and pulverized adsorbents), relates to larger micropores and predominantly smaller mesopores and gives an indication of the adsorptive capacity of the high-performance adsorbents of the present invention in relation to molecules comparable in size to methylene blue. By contrast, the molasses number must be considered a measure of the meso- and macroporosity and indicates the amount of adsorbents which is required to decolorize a standard molasses solution, so that the molasses number gives an indication of the adsorptive capacity of the high-performance adsorbents of the present invention in relation to molecules that are comparable in size to molasses (generally sugar beet molasses). Together, therefore, the methylene blue and molasses numbers can be considered a measure of the meso- and macroporosity of the high-performance adsorbents of the present invention.

The methylene blue value of the high-performance adsorbents of the present invention which is determined by following the method of CEFIC (Conseil Européen des Féderations des Industries Chimiques, Avenue Louise 250, Bte 71, B-1050 Brussels, November 1986, European Council of Chemical Manufacturers' Federations, Test Methods for Activated Carbons, Item 2.4 "Methylene blue value", pages 27/28) is at least 15 ml, particularly at least 17 ml, preferably at least 19 ml, and is generally in the range from 15 to 60 ml, particularly 17 to 50 ml, preferably 19 to 45 ml.

The methylene blue value according to the aforementioned CEFIC method is thus defined as the number of ml of a methylene blue standard solution which are decolorized by 0.1 g of dry and pulverized activated carbon. Performing this method requires a glass vessel with ground stopper, a filter and also a methylene blue standard solution prepared as follows: 1200 mg of pure methylene blue dye (corresponding to about 1.5 g of methylene blue to DAB VI [German Pharmacopeia, 6th edition] or equivalent product) are dissolved in water in a 1000 ml volumetric flask, and the solution is allowed to stand for several hours or overnight; to check its strength, 5.0 ml of the solution are diluted with 0.25% (volume fractions) acetic acid to 1.01 in a volumetric flask and thereafter the absorbance is measured at 620 nm and 1 cm path length, and it has to be 0.840±0.010. If the absorbance is higher, it has to be diluted with the computed amount of water; if it is lower, the solution is discarded and made up fresh. By way of sample preparation, the high-performance adsorbents in the form of granular activated carbon are pulverized (<0.1 mm) and then dried to a constant weight at 150° C. Precisely 0.1 g of the spherocarbon is then combined with 25 ml (5 ml) of the methylene blue standard solution in a ground glass flask (A preliminary test has to be carried out to see whether an initial addition of 25 ml of methylene blue standard solution with 5 ml additions or an initial addition of 5 ml of methylene blue standard solution with 1 ml additions can be used.). The flask is shaken until decolorization occurs. Then, a further 5 ml (1 ml) of the methylene blue standard solution are added, and the flask is shaken to the point of decolorization. The addition of methylene blue standard solution is repeated in 5 ml amounts (1 ml amounts) as long as decolorization still occurs within 5 minutes. The entire volume of the test solution decolorized by the sample is recorded. The test is repeated to confirm the results obtained. The volume of the methylene blue standard solution in ml which are just decolorized is the methylene blue value of the high-performance adsorbents. It is to be noted in this connection that the methylene blue dye must not be dried, since it is heat sensitive; rather, the water content must be corrected for purely arithmetically.

The dimensionless molasses number can in principle be determined either by following the Norit method (Norit N.V., Amersfoort, Netherlands, Norit Standard Method NSTM 2.19 "*Molasses Number (Europe)*") or alternatively by following the PACS method (PACS=Professional Analytical and Consulting Services Inc., Coraopolis Pa., USA). In the context of the present invention, the values of the molasses number are determined by following the PACS method. Thus, the PACS method molasses number of the high-performance adsorbents of the present invention is at least 300, particularly at least 350, preferably at least 400, and is generally in the range from 300 to 1400, particularly 350 to 1300, preferably 400 to 1250, most preferably 700 to 1200.

Whether by following the Norit method or by following the PACS method, the molasses number is determined by determining the amount of pulverized high-performance adsorbents based on activated carbon that is needed to decolorize a standard molasses solution. Determination is effected photometrically, and the standard molasses solution is standardized against a standardized activated carbon having a molasses number of 245 and/or 350. For further details in this regard, reference can be made to the two aforementioned prescriptive methods.

Despite their high porosity, particularly meso- and macroporosity, the high-performance adsorbents of the present invention have a high compressive or bursting strength (resistance to weight loading) and also an extremely high abrasion resistance.

The compressive or bursting strength (resistance to weight loading) per grain of activated carbon, in particular per spherule of activated carbon, is thus at least 5 newtons, in particular at least 10 newtons and preferably at least 15 newtons. In general, the compressive or bursting strength (resistance to weight loading) per grain of activated carbon, particularly per spherule of activated carbon, ranges from 5 to 50 newtons, in particular from 10 to 45 newtons and preferably from 15 to 40 newtons.

As mentioned, the abrasion hardness of the high-performance adsorbents of the present invention is also extremely high in that the abrasion resistance when measured by the method of CEFIC (Conseil Européen des Féderations des Industries Chimiques, Avenue Louise 250, Bte 71, B-1050 Brussels, November 1986, European Council of Chemical Manufacturers' Federations, Test Methods for Activated Carbons, Item 1.6 "Mechanical Hardness", pages 18/19) is always 100% or virtually 100%. Similarly, when measured according to ASTM D3802 abrasion resistances of the high-performance adsorbents of the present invention of 100% or virtually 100% are always obtained.

Therefore, the applicant company has developed a modified test method on the lines of this CEFIC method in order that more meaningful values may be obtained. The modified method of determination provides a better simulation of the resistance of the sample or to be more precise of the high-performance adsorbents to abrasion or attrition under near actual service conditions. For this purpose, the sample is exposed to standardized conditions for a defined time in a horizontally swinging grinding cup charged with a tungsten carbide ball. The procedure adopted for this purpose is as follows: 200 g of a sample are dried for one hour at (120±2°) C. in a circulating air drying cabinet (type: Heraeus UT 6060 from Kendro GmbH, Hanau) and are subsequently cooled down in a desiccator over drying agent to room temperature. 50 g of the dried sample are removed and sieved off by means of a sieving machine equipped with an analytical sieve (for example, type: AS 200 control from Retsch GmbH, Hanau) at a swing amplitude of 1.2 mm for ten minutes through an analytical sieve, the analytical sieve being selected depending on the grain distribution of the sample to be measured (for example, analytical sieve of mesh size: 0.315 mm, diameter: 200 mm, height: 50 mm); the subsize grain is discarded. 5 ml of the nominal grain are filled into a 10 ml graduated cylinder to DIN ISO 384 (volume: 10 ml, height: 90 mm) and the weight is accurately determined to 0.1 mg using an analytical balance (type: BP121S from Sartorius A G, Göttingen, weighing range: 120 g, accuracy class: E2, readability: 0.1 mg) by means of a weighing glass having a ground glass lid (volume: 15 ml, diameter: 35 mm, height: 30 mm). The weighed sample is placed together with a tungsten carbide grinding ball of 20 mm diameter in a 25 ml grinding cup with screw action closure (volume: 25 ml, diameter: 30 mm, length: 65 mm, material of construction: stainless steel) and then the abrasion test is carried out by means of a swing mill (type: MM301 from Retsch GmbH, Haan, swing mill with grinding cup); the grinding cup swings in a horizontal position for one minute at a frequency of 10 Hz in the swing mill, causing the grinding ball to impact on the sample and thus create abrasion. Subsequently, the sample is sieved off by means of a sieving machine at a swing amplitude of 1.2 mm for five minutes through the aforementioned analytical sieve, the subsize grain again being discarded and the nominal grain, which is dependent on the grain distribution of the relevant sample (e.g. nominal grain greater than 0.315 mm), being weighed back accurately to 0.1 mg in the weighing glass with lid. The abrasion hardness is computed as a mass fraction in % by the following formula: abrasion hardness [%]=(100× back-weighed weight [g])/original weight [g].

According to this method of determination, modified by the applicant company by modifying the aforementioned CEFIC standard, the abrasion resistance of the high-performance adsorbents of the present invention is at least 75%, particularly at least 80%, preferably at least 85%, more preferably at least 90%, most preferably at least 95%.

As stated above, it is a further special feature of the high-performance adsorbents of the present invention that they also have a certain degree of microporosity and thus also a certain micropore surface area (i.e. surface area which is formed by pores having pore diameters of ≤20 Å. In general, the carbon black method micropore surface area of the high-performance adsorbents of the present invention which is formed by pores having pore diameters of ≤20 Å is at least 1000 m$^2$/g, particularly at least 1100 m$^2$/g, preferably at least 1200 m$^2$/g, and is generally in the range from 1000 to 1800 m$^2$/g, particularly 1100 to 1600 m$^2$/g, preferably 1200 to 1500 m$^2$/g.

In general, the carbon black method micropore surface area of the high-performance adsorbents of the present invention which is formed by pores having pore diameters of ≤20 Å is at least 30%, particularly at least 40%, preferably at least 50% of the total pore surface area of the high-performance adsorbents of the present invention. More particularly, the carbon black method micropore surface area of the high-performance adsorbents of the invention which is formed by pores having pore diameters of ≤20 Å is in the range from 50 to 90%, particularly 55 to 85%, preferably 60 to 80% of the total pore surface area of the high-performance adsorbents of the present invention.

Similarly, the weight- and volume-based volume $V_{ads}$ ($N_2$) of the high-performance adsorbents of the present invention at different partial pressures $p/p_0$ is very large:

The weight-based adsorbed $N_2$ volume $V_{ads(wt)}$ of the high-performance adsorbents of the present invention, determined at a partial pressure $p/p_0$ of 0.25, is at least 300 cm$^3$/g, particularly at least 350 cm$^3$/g, preferably at least 375 cm$^3$/g, and is particularly in the range from 300 to 800 cm$^3$/g, preferably 350 to 700 cm$^3$/g, more preferably 375 to 650 cm$^3$/g.

In general, the volume-based adsorbed $N_2$ volume $V_{ads(vol)}$ of the high-performance adsorbents of the present invention, determined at a partial pressure $p/p_0$ of 0.25, is at least 75 cm$^3$/cm$^3$, particularly at least 100 cm$^3$/cm$^3$, and is particularly in the range from 75 to 300 cm$^3$/cm$^3$, preferably 80 to 275 cm$^3$/cm$^3$, more preferably 90 to 250 cm$^3$/cm$^3$.

In general, the weight-based adsorbed $N_2$ volume $V_{ads(wt)}$ of the high-performance adsorbents of the present invention, determined at a partial pressure $p/p_0$ of 0.995, is at least 400 cm$^3$/g, particularly at least 450 cm$^3$/g, and is particularly in the range from 400 to 2300 cm$^3$/g, preferably 450 to 2200 cm$^3$/g, more preferably 750 to 2100 cm$^3$/g.

In general, the volume-based adsorbed $N_2$ volume $V_{ads(vol)}$ of the high-performance adsorbents of the present invention, determined at a partial pressure $p/p_0$ of 0.995, is at least 200 cm$^3$/cm$^3$, particularly at least 250 cm$^3$/cm$^3$, and is particularly in the range from 200 to 500 cm$^3$/cm$^3$, preferably 250 to 400 cm$^3$/cm$^3$, more preferably 275 to 380 cm$^3$/cm$^3$.

The high-performance adsorbents of the present invention are based on granular, in particular spherical, activated carbon whose measure of central tendency particle diameter, determined to ASTM D2862-97/04, is generally in the range from 0.01 to 2.0 mm, particularly 0.01 to 1.0 mm, preferably 0.05 to 0.09 mm, more preferably 0.1 to 0.8 mm, most preferably 0.15 to 0.7 mm.

The ash content of the high-performance adsorbents of the present invention, determined to ASTM D2866-94/04, is at most 1%, particularly at most 0.8%, preferably at most 0.6%, more preferably at most 0.5%.

The ASTM D2867-04/04 moisture content of the high-performance adsorbents of the present invention is at most 1%, particularly at most 0.5%, preferably at most 0.2%.

The high-performance adsorbents of the present invention generally have a bulk density, determined to ASTM B527-93/00, in the range from 150 to 750 g/l, particularly 175 to 650 g/l, preferably 200 to 600 g/l.

In accordance with a particular embodiment of the present invention, the present invention provides high-performance adsorbents based on activated carbon in the form of discrete grains of activated carbon, preferably in spherical form, particularly as described above, characterized by the following parameters:
- a pore volume fraction formed by pores having pore diameters of more than 20 Å which comprises at least 55% of the total pore volume of the high-performance adsorbents,
- a measure of central tendency pore diameter of more than 25 Å.
- a BET surface area of at least 1250 m$^2$/g,
- a methylene blue value of at least 15 ml, and
- a molasses number of at least 300.

The present invention further provides—in accordance with a second aspect of the present invention—the present invention process for producing the high-performance adsorbents according to the present invention. In accordance with this aspect of the present invention, the present invention accordingly provides a process for producing the above-described high-performance adsorbents based on activated carbon, which process comprises a carbonaceous starting material being initially carbonized and subsequently activated, wherein the activation is carried out in two stages, wherein the carbonized starting material is initially subjected, in a first activating step, to an activation in an atmosphere comprising water vapor, followed by a second activating step of activation in an atmosphere comprising $CO_2$.

The high-performance adsorbents of the present invention are produced using carbonaceous starting materials, in particular sulfonated styrene-divinylbenzene copolymers, particularly sulfonated divinylbenzene-crosslinked polystyrenes, preferably in grain form, more preferably in spherical form. The divinylbenzene content of the sulfonated styrene-divinylbenzene copolymers used as starting materials to produce the high-performance adsorbents of the present invention should particularly be in the range from 1 to 20% by weight, particularly 1 to 15% by weight, preferably 2 to 10% by weight, based on the styrene-divinylbenzene copolymers. The starting copolymers can in principle be selected from the gel type or else from the macroporous type. When unsulfonated starting materials are used, the sulfonation can be carried out in situ (in particular before and/or during the carbonization), particularly using methods known per se to one skilled in the art, preferably by means of sulfuric acid and/or oleum and/or $SO_3$; this is familiar per se to one skilled in the art (cf. also the prior art described at the beginning). Starting materials which have proven particularly advantageous are the gel-form or macroporous types of the corresponding ion exchange resins or of the corresponding unsulfonated precursors of ion exchange resins which still have to be sulfonated.

The carbonization (also known by the synonyms of pyrolysis, burn-out or smoldering) converts the carbonaceous starting polymers to carbon; that is, in other words, the carbonaceous starting material is carbonized. Carbonization of the aforementioned organic polymeric grains, in particular polymeric spherules, based on styrene and divinylbenzene which comprise sulfonic acid groups leads to the detachment of the sulfonic acid groups during the carbonization to free radicals and thus to crosslinks without which there would be no pyrolysis residue (=carbon). In general, the carbonization is carried out under an inert atmosphere (for example nitrogen) or an at most slightly oxidizing atmosphere. It can similarly be advantageous for the inert atmosphere of the carbonization, in particular if it is carried out at comparatively high temperatures (for example in the range from about 500 to 650° C.) to be admixed with a minor amount of oxygen, in particular in the form of air (for example 1 to 5%) in order that an oxidation of the carbonized polymeric skeleton may be effected and the subsequent activation may thereby be facilitated. In general, the carbonization is carried out at temperatures of 100 to 950° C., particularly 150 to 900° C., preferably 300 to 850° C. The total duration of the carbonization is approximately 30 minutes to approximately 10 hours, particularly approximately 1 hour to approximately 6 hours.

Following the carbonization, the carbonized intermediate product is subjected to an activation resulting, at the end of which, in the present invention's high-performance adsorbents based on activated carbon in grain form, in particular spherical form. The basic principle of the activation is to degrade a portion of the carbon generated during the carbonization, selectively and specifically under suitable conditions. This gives rise to numerous pores, fissures and cracks, and the surface area per unit mass increases appreciably. Activation thus involves a specific burn-out of the carbon. Since carbon is degraded in the course of activation, this operation goes hand in hand with a loss of substance which—under optimal conditions—is equivalent to an increase in the porosity and in the internal surface area and in the pore volume. Activation is therefore carried out under selective or to be more precise policed oxidizing conditions.

The special feature of how the high-performance adsorbents of the present invention are produced, as well as the selection of the starting material described above, resides in the specific management of the activation process, in particular in the two-stageness of the activation process, wherein the carbonized starting material is initially subjected, in a first activating step, to an activation in an atmosphere comprising water vapor, followed by a second activating step in an atmosphere comprising $CO_2$. As the studies carried out by the applicant have determined it is surprisingly only the separate performance of these activating steps in the aforementioned order that leads to the desired products. Reversing the order of the activating steps, or one conjointly conducted activating step in a water vapor/carbon dioxide atmosphere leads in contrast to distinctly less performance-capable products which do not have the desired properties, particularly not the high total porosity coupled with high meso-/macropore content and a relatively high absolute micropore volume and also high mechanical stability. As the studies by the applicant company have surprisingly shown when the process is carried out according to the present invention water vapor activation leads predominantly to the formation of the micropore fraction, while carbon dioxide activation contributes predominantly to formation of the meso- and macropores, and surprisingly the formation of the meso- and macropore volume is not at the expense of the micropore volume, or vice versa. What is therefore novel and surprising is in total that this produces a very large total pore volume coupled with very high stability and abrasion resistance and also very high meso- and macropore fraction coupled with simultaneously high micropore fraction (i.e., the formation of meso- and macropores to the enormous extent in the products of the present invention does not lead to a reduction in the micropore fraction, as customary in the prior art). On the contrary, a high micropore fraction is achieved while the meso-/macropore volume fraction is also high at the same time.

The general procedure is for the first activating step to be carried out at temperatures of 700 to 1300° C., particularly 800 to 1200° C., preferably 850 to 950° C., and/or for a duration of 5 to 24 hours, preferably 5 to 15 hours, particularly 6 to 12 hours. Usually, the duration of the first activation stage can be controlled as a function of the attainment of a predetermined iodine number; for example, the first activation stage can be carried out to attainment of an iodine number of at least 1000 mg/g, particularly at least 1250 mg/g. The atmosphere of the first activation stage comprises water vapor, particularly a mixture of water vapor/inert gas, preferably a mixture of water vapor/nitrogen, or consists thereof. For the aforementioned reasons, the presence of activating gases other than water vapor, particularly the presence of carbon oxides ($CO_2$ for example), oxygen and/or ammonia, must be foreclosed in the context of the first activation stage. Good results are obtained when the throughput or to be more precise the amount used of water vapor is 25 to 350 l/h, particularly 50 to 300 l/h, reckoned as water (i.e., liquid water at 25° C. and under atmospheric pressure). Depending on the amount of starting material to be activated (=carbonisate previously produced by carbonization), the amount used or the mass-based throughput of water vapor should advantageously be 0.01 to 50 l/(h·kg), particularly 0.02 to 25 l/(h·kg), preferably 0.02 to 5 l/(h·kg), reckoned as water (i.e., liquid water at 25° C. and under atmospheric pressure) and based on starting material to be activated with water vapor.

The general procedure for the second activating step is for the second activating step to be carried out at temperatures of 700 to 1300° C., particularly 800 to 1200° C., preferably 850 to 950° C., and/or for a duration of 1 to 10 hours, particularly 3 to 8 hours. The atmosphere of the second activation stage comprises $CO_2$, particularly pure $CO_2$ or a mixture of $CO_2$/inert gas, particularly a mixture of $CO_2$/nitrogen, or consists thereof, and pure carbon dioxide is particularly preferred. For the aforementioned reasons, the presence of activating gases other than $CO_2$, in particular the presence of water vapor, must be foreclosed in the context of the second activation stage. Good results are obtained when the throughput or the amount used of $CO_2$ is 10 to 250 m³/h, particularly 20 to 200 m³/h (based on pure $CO_2$). Depending on the amount of starting material to be activated, the amount used or the mass-based throughput of $CO_2$ should advantageously be 0.001 to 100 m³/(h·kg), particularly 0.01 to 50 m³/(h·kg), preferably 0.05 to 10 m³/(h·kg), reckoned as pure gaseous $CO_2$ under activating conditions, particularly at the respective pressure and the respective temperature, which are selected for the activation, and based on starting material to be activated with $CO_2$.

The process is typically carried out such that the first and second activation stages merge into each other (for example by changing the activating atmosphere within the same apparatus).

What is surprising is in particular that, first, the way the activation is carried out according to the present invention provides exact control of the porosity with regard to the micro-, meso- and macropore fractions and, secondly, that an extremely high abrasion resistance and mechanical compressive strength result despite the high porosity coupled with simultaneously high meso- and macroporosity and also good microporosity. It was unforeseeable that this approach selectively generates high meso- and macroporosity coupled with simultaneously sufficient microporosity.

Porosity can be adjusted or controlled to specific values by varying the previously specified activating conditions. The high-performance adsorbents of the present invention can thus be custom tailored so to speak. High-performance adsorbents based on activated carbon which combine high meso- and macroporosity with good microporosity and also high stability and abrasion resistance are not known from the prior art. Another welcome aspect is the excellent adsorption behavior to molecules of virtually any desired molecular size due to the presence of all kinds of pores in relatively large amounts or fractions. Similarly welcome is the excellent impregnatability of the products of the present invention with catalysts or to be more precise metals or metal salts.

Figure 2:
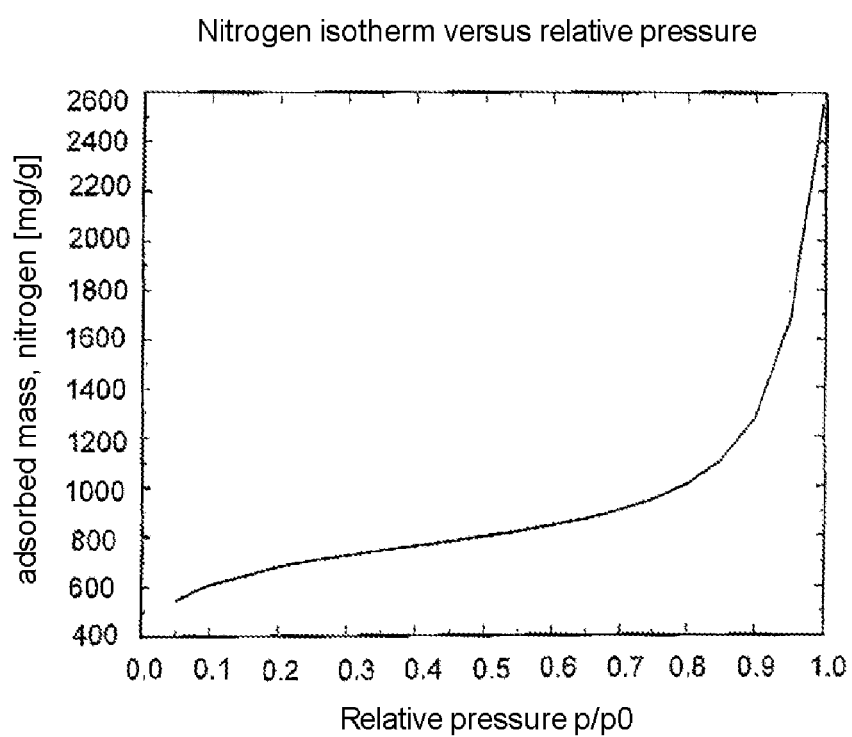
FIG. 2 is a graph illustrating a $N_2$ adsorption isotherm for a second high-performance adsorbent of the present invention.

The graphs in FIG. 1 and FIG. 2 show $N_2$ adsorption isotherms for two different high-performance adsorbents of the present invention, which were produced under different activating conditions. The physical-chemical properties of the two high-performance adsorbents of the present invention are also summarized in Table 1 below. For comparison, a commercially available activated carbon from Kureha is also listed therein with the physical-chemical properties in question.

The data reported in Table 1 show the superiority of the high-performance adsorbents of the present invention over a prior art activated carbon: The combination of high total porosity with high meso-/macropore volume fraction at high BET surface area and also good absolute microporosity, high mechanical durability and excellent adsorption properties is in this combination—as well as the other physical-chemical parameters—only to be found in the high-performance adsorbents of the present invention. The present invention thus makes it possible to produce high-performance adsorbents based on activated carbon in grain form, in particular spherical form, which are superior to commercially available products.

The inventive high-performance adsorbents "activated carbon I" and "activated carbon II" recited in Table 1 are each produced as follows: commercially available dried ion exchanger precursors based on divinylbenzene-crosslinked polystyrene copolymers having a divinylbenzene content of about 4% are sulfonated in a conventional manner at temperatures of 100° C. to 150° C. using a sulfuric acid/oleum mixture. This is followed in a conventional manner by carbonization at temperatures up to 850° C. for four hours under nitrogen and subsequently the induction of activation. Inventive activated carbon I was produced by performing the first activation stage ("water vapor activation") for a duration of about 8.5 hours at about 900° C. with a water vapor throughput of about 100 m³/h and the second activation stage ("carbon dioxide activation") for a duration of about 8.0 hours at about 900° C. with a carbon dioxide throughput of about 35 m³/h; in contrast, inventive activated carbon II was produced by performing the first activation stage ("water vapor activation") for a duration of about 10.5 hours at about 925° C. with a water vapor throughput of about 125 m³/h and the second activation stage ("carbon dioxide activation") for a duration of about 8 hours at about 925° C. with a carbon dioxide throughput of about 40 m³/h. After cooling down to room temperature, the inventive products recited in Table 1 are obtained.

TABLE 1

Comparison of physical-chemical parameters of two inventive high-performance adsorbents based on spherical activated carbon on the one hand and commercially available activated carbon in spherical form from Kureha on the other

|  | Inventive activated carbon I | | Inventive activated carbon II | | Commercially available activated carbon from Kureha |
| --- | --- | --- | --- | --- | --- |
|  | After first activating step (intermediate product) | After second activating step (end product) | After first activating step (intermediate product) | After second activating step (end product) | |
| Total pore volume (Gurvich) ($p/p_0$ = 0.995) [$cm^3/g$]** | 0.6267 | 1.7890 | 0.7510 | 3.1590 | 0.5891 |
| Measure of central tendency pore diameter [Å] | 18.08 | 42.05 | 19.05 | 62.75 | 17.89 |
| BET (Multipoint, MP) ($p/p_0$ = 0.05-0.1) (ASTM D6556-04) [$m^2/g$]** | 1.387 | 1.702 | 1.577 | 2.013 | 1.317 |
| Carbon black method micropore volume [$cm^3/g$]* | 0.5524 | 0.5082 | 0.6211 | 0.5311 | 0.5240 |
| Micropore fraction of total pore volume [%]* | 88.1 | 28.4 | 82.7 | 16.8 | 88.95 |
| Adsorbed $N_2$ volume ($p/p_0$ = 0.25) weight based [$cm^3/g$]** | 368 | 463 | 422 | 563 | 349 |
| Adsorbed $N_2$ volume ($p/p_0$ = 0.25) volume based [$cm^3/cm^3$]** | 233 | 138 | 227 | 101 | 206 |
| Adsorbed $N_2$ volume ($p/p_0$ = 0.995) weight based [$cm^3/g$]** | 404 | 1154 | 484 | 2037 | 380 |
| Adsorbed $N_2$ volume ($p/p_0$ = 0.995) volume based [$cm^3/cm^3$]** | 256 | 344 | 261 | 365 | 224 |
| Carbon black micropore surface area [$cm^2/g$]* | 1342 | 1261 | 1499 | 1288 | 1271 |
| Carbon black meso-plus macropore volume (= so-called external pore volume) [$cm^3/g$]*** | 0.0743 | 1.2808 | 0.1299 | 2.6279 | 0.07 |
| Fraction of meso-and macropores in total pore volume (= fraction of so-called external pore volume in relation to total pore volume) [%]*** | 11.9 | 71.6 | 17.3 | 83.2 | 11.1 |
| Carbon black surface area of meso- and macropores (= so-called external pore surface area) [$cm^2/g$]*** | 45 | 441 | 78 | 725 | 46 |
| Pore surface area fraction of meso- and macropores in relation to BET surface area (= proportion of so-called external pore surface area in relation to BET surface area) (MP) [%]*** | 3.2 | 25.9 | 4.9 | 36.0 | 3.5 |
| Adsorbate | $N_2$ | $N_2$ | $N_2$ | $N_2$ | $N_2$ |
| Butane adsorption (ASTM D5742-95/00) [%] | 30.9 | 42.4 | 35.4 | 52.9 | 29.2 |
| Iodine number (ASTM D4607-94/99) [mg/g] | 1413 | 1588 | 1490 | 1750 | 1343 |
| Methylene blue number (CEFIC) [ml] | 19.9 | 34.8 | 27.2 | 38.9 | <10 |
| Molasses number (PACS) [dimensionless] | 96 | 1020 | 142 | 1174 | <100 |
| Abrasion resistance (internal method) [%] | 98.22 | 90.38 | 99.2 | 90.04 | <90 |

*micropores: pores having pore diameters ≤20 Å
**$p/p_0$ = partial pressure or partial pressure range
***meso-and macropores: collective term for all pores with pore diameters >20 Å

The present invention further provides—in accordance with a third aspect of the present invention—the present invention use of the high-performance adsorbents according to the present invention.

The high-performance adsorbents of the present invention are particularly useful for the adsorption of toxins, noxiants and odors, for example from gas or to be more precise air streams. The high-performance adsorbents of the present invention are further useful for purifying and cleaning gases, particularly for purifying air, and also liquids, such as, in particular, water (for example drinking water treatment). More particularly, the high-performance adsorbents of the present invention are useful for impregnation (for example with catalysts or to be more precise metals or metal salts).

The high-performance adsorbents of the present invention are also useful for example for or in the food industry, particularly for preparing and/or decolorizing food products.

The high-performance adsorbents of the present invention can further be used in adsorptive filtering materials or to be more precise in the manufacture of adsorptive filtering materials. Such adsorptive filtering materials are useful in the manufacture of protective apparel in particular, for example protective suits, protective gloves, protective underwear, protective footwear, etc., in particular for the civilian or military sector (for example NBC protection).

The high-performance adsorbents of the present invention are further useful in the sector of medicine or pharmacy, particularly as a medicament or medicament constituent.

The high-performance adsorbents of the present invention can finally also be used as sorptive storage media for gases and liquids.

Owing to their high total porosity coupled with high meso- and macroporosity and similarly a certain degree of microporosity and also excellent mechanical stability with excellent adsorptive properties, the high-performance adsorbents of the present invention are distinctly superior to comparable adsorbents of the prior art.

Further embodiments, modifications and variations of the present invention are readily discernible and realizable for those skilled in the art on reading the description without their having to leave the realm of the present invention. While the invention has been illustrated and described in detail in the drawings and foregoing description, the same is to be considered as illustrative and not restrictive in character, it being understood that only the preferred embodiment has been shown and described and that all changes and modification that come within the spirit of the invention are desired to be protected.

We claim:

1. A process for producing the high-performance adsorbents based on activated carbon,
   which high-performance adsorbents are in the form of discrete grains of activated carbon and which high-performance adsorbents are characterized by the following properties:
   at least 70% of the total pore volume of the high-performance adsorbents is formed by pores having pore diameters of more than 20 Å,
   the mean pore diameter of the high-performance adsorbents is more than 25 Å,
   the BET surface area of the high-performance adsorbents is at least 1,250 m$^2$/g, and
   the iodine number of the high-performance adsorbents is at least 1,250 mg/g;
   which process comprises the following steps:
   a carbonaceous starting material is initially carbonized and subsequently activated, wherein the carbonaceous starting material comprises sulfonated styrene-divinylbenzene copolymers,
   wherein the activation is carried out in two stages, wherein, in a first activating step, the carbonized starting material is initially subjected to an activation in an atmosphere comprising water vapor, wherein the mass-based throughput of water vapor is 0.01 to 50 l/(h·kg), calculated as pure water and based on the amount of starting material to be activated with water vapor, followed by a second activating step of activation in an atmosphere comprising $CO_2$,
   wherein the mass-based throughput of $CO_2$ is 0.001 to 100 m$^3$/(h·kg), calculated as pure gaseous $CO_2$ under activating conditions and based on the amount of starting material to be activated with $CO_2$.

2. The process as claimed in claim 1,
   wherein carbonization is carried out at temperatures in the range of from 100 to 950° C. and for a duration of 0.5 to 6 hours.

3. The process as claimed in claim 1,
   wherein carbonization is carried out under an inert or at most slightly oxidizing atmosphere.

4. The process as claimed in claim 1,
   wherein the high-performance adsorbents are further characterized by at least one of the further following properties:
   a Gurvich total pore volume of the high-performance adsorbents of at least 0.8 cm$^3$/g and up to 3.5 cm$^3$/g,
   a carbon black method pore volume of the high-performance adsorbents which is formed by pores having pore diameters of more than 20 Å in the range of from 0.4 to 3.3 cm$^3$/g,
   a butane adsorption of the high-performance adsorbents in the range from 30 to 80%,
   a methylene blue value of the high-performance adsorbents in the range from 15 to 60 ml,
   a molasses number of the high-performance adsorbents in the range from 300 to 1,400;
   an iodine number of the high-performance adsorbents in the range from 1,250 to 2,100 mg/g.

5. The process as claimed in claim 1,
   wherein the atmosphere of the first activating step comprises water vapor, wherein the mass-based throughput of water vapor is 0.02 to 25l/(h·kg), calculated as pure water and based on the amount of starting material to be activated with water vapor.

6. The process as claimed in claim 1,
   wherein the atmosphere of the first activating step comprises water vapor in the form of a mixture of water vapor and an inert gas.

7. The process as claimed in claim 1,
   wherein the first activating step is carried until a predetermined iodine number of at least 1,000 mg/g is attained.

8. The process as claimed in claim 1,
   wherein the first activating step is carried out at temperatures of from 700 to 1,300° C. and for a duration of 5 to 24 hours.

9. The process as claimed in claim 1,
   wherein the first activating step is carried out at temperatures of from 800 to 1,200° C. and for a duration of 6 to 15 hours.

10. The process as claimed in claim 1,
    wherein the atmosphere of the first activating step comprises water vapor in the form of a mixture of CO2 and an inert gas.

11. The process as claimed in claim 1,
    wherein the second activating step is carried out at temperatures of from 700 to 1,300° C. and for a duration of 1 to 10 hours.

12. The process as claimed in claim 1,
    wherein the second activating step is carried out at temperatures of from 800 to 1,200° C. and for a duration of 3 to 8 hours.

13. The process as claimed in claim 1,
    wherein the atmosphere of the second activating step comprises CO2, wherein the mass-based throughput of CO2 is 0.01 to 50 m$^3$/(h·kg), calculated as pure gaseous CO2 under activating conditions and based on the amount of starting material to be activated with CO2.

* * * * *